United States Patent [19]

Flower

[11] Patent Number: 5,394,199
[45] Date of Patent: Feb. 28, 1995

[54] METHODS AND APPARATUS FOR IMPROVED VISUALIZATION OF CHOROIDAL BLOOD FLOW AND ABERRANT VASCULAR STRUCTURES IN THE EYE USING FLUORESCENT DYE ANGIOGRAPHY

[75] Inventor: Robert W. Flower, Hunt Valley, Md.

[73] Assignee: The Johns Hopkins University, Baltimore, Md.

[21] Appl. No.: 63,343

[22] Filed: May 17, 1993

[51] Int. Cl.$^6$ .......................... A61B 3/12; A61B 3/14; A61B 5/02

[52] U.S. Cl. .................................... 351/206; 351/205; 351/215; 351/221; 128/633; 128/666; 128/691; 128/745

[58] Field of Search ............... 351/200, 205, 211, 216, 351/221, 245, 206, 215; 128/664, 665, 666, 691, 745, 633; 606/4

[56] References Cited

U.S. PATENT DOCUMENTS

| | | | |
|---|---|---|---|
| 3,893,447 | 7/1975 | Hochheimer et al. | 351/206 |
| 5,150,292 | 9/1992 | Hoffmann et al. | 128/691 |
| 5,225,859 | 7/1993 | Fleischman | 351/206 |
| 5,247,318 | 9/1993 | Suzuki | 351/206 |
| 5,279,298 | 1/1994 | Flower | 128/633 |
| 5,303,709 | 4/1994 | Dreher et al. | 351/221 X |

*Primary Examiner*—William L. Sikes
*Assistant Examiner*—David R. Parsons
*Attorney, Agent, or Firm*—Francis A. Cooch

[57] ABSTRACT

A method for visualizing the choriocapillaris of the eye in a sequence of ICG angiographic images comprising subtracting each image in the angiographic sequence from a succeeding image. In practice, a modified fundus camera is used to provide digitized images which are subtracted pixel by pixel. To better visualize aberrant vascular structures such as choroidal neovascularization (CNV), a fundus camera is modified with a polarizing filter in front of the light source and an analyzing polarizer in front of the video camera. This results in the suppression of unwanted scattered fluorescence to the extent that the CNV can be better visualized. To assist the surgeon in treating aberrant vascular structures with laser photocoagulation therapy, a fundus camera is provided with two light sources and two barrier filters operating synchronously to produce and pass two different fluorescences thereby generating precisely superimposable angiographs to aid in aiming the laser.

30 Claims, 7 Drawing Sheets

METHODS AND APPARATUS FOR IMPROVED VISUALIZATION OF CHOROIDAL BLOOD FLOW AND ABERRANT VASCULAR STRUCTURES IN THE EYE USING FLUORESCENT DYE ANGIOGRAPHY

BACKGROUND OF THE INVENTION

There is very little information about the blood flow through capillary plexuses which occurs on the time scale of the cardiac cycle. In part this is because direct visualization of such plexuses usually is technologically difficult or impossible, and most blood flow measurement methodologies require that data be obtained over many cardiac cycles. Moreover, when the capillary plexuses have complex vascular geometries and are fed by many arterioles, the additional problem of sorting-out blood flow distributions arises. One example of a capillary plexus is that found in the cerebral cortex. Another example, of great interest to scientists studying the eye, is the choriocapillaris, one of three blood vessel layers of the choroid.

The choroidal circulation of the eye bears a major responsibility for maintaining the sensory retina which lies above it. A prior art method has made possible routine visualization of the entire choroidal circulation, that is, all three vessel layers of the choroid can be visualized, superimposed one above the other. The innermost layer, the choriocapillaris, constitutes all of the nutritive vessels (i.e., where metabolic exchange with the retina takes place) for the choroidal circulation. The choriocapillaris layer occupies the plane immediately adjacent to the sensory retina.

Although choroidal angiograms show all of the vessels of the choroid, information pertaining specifically to the choriocapillaris is the most important, and there are conflicting views about the organization of the posterior pole choriocapillaris, particularly concerning blood flow through it. The method of extracting information about the choriocapillaris from an indocyanine green (ICG) angiogram is therefore an important one to the clinician who is interested in evaluating the metabolic sufficiency and stability of the choroidal circulation.

Numerous investigators have used angiography and a variety of histological techniques to collect the current body of information about the choroidal circulation. Although the gross aspects of choroidal angioarchitecture and blood flow have been amply revealed by investigators' efforts, controversies still exist regarding regional differences in morphology. Additional controversies have also arisen regarding details of blood flow through this highly complicated vascular network.

Of particular interest is blood flow through the choriocapillaris, since, as discussed above, it is in this vascular layer that the nutritive function of the choroidal circulation takes place. Even though the state of the larger choroidal blood vessels must certainly influence choriocapillaris blood flow, ultimately it is a precise understanding of the choriocapillaris blood flow itself that is fundamental to understanding the choroid's role in the pathophysiology of retinal disease.

High-speed indocyanine green (ICG) dye fluorescence angiography was developed to overcome the major problems encountered when attempting to visualize the rapid choroidal blood flow encountered in sodium fluorescein angiography. ICG angiography utilizes near-infrared wavelengths which penetrate the retinal pigment epithelium and choroidal pigment with relative ease. Whereas fluorescence from the choriocapillaris resulting from intravenously injected sodium fluorescein dye (the other standard dye used in ocular angiography) appears to arise mainly from extravasated dye molecules or those adhering to the vessel walls, ICG fluorescence arises from dye molecules bound to blood protein in the moving blood volume.

No doubt scanning laser ophthalmoscope fluorescein angiography (which can also utilize ICG dye) and the experimental technique of injecting fluorescein encapsulated in lipid vesicles eventually will produce additional information about choroidal blood flow; but with respect to clinical choroidal angiography, ICG angiography provides the best temporal and spatial resolution, making visualization of dye passage through the choroid possible under normal physiological conditions (i.e., without having to artificially slow blood flow by such methods as raising intraocular pressure).

When making intravenous dye injections, however, it is difficult to observe the choriocapillaris in individual ICG angiogram images due to the much higher levels of fluorescence arising from the large diameter underlying vessels. Due to this multi-layered organization of the choroidal vasculature, observation of the choriocapillaris with fluorescent dye angiography is best accomplished when a very small volume dye bolus having a sharply defined wavefront passes through. For example, following intra-carotid injection of a very small ICG dye bolus, ICG angiograms have been produced which clearly show the complete cycle of dye passage through an individual lobule under normal physiologic conditions. (Lobule is a term used to denote the three- to six-sided vascular units which form a mosaic pattern throughout the choriocapillaris. Each lobule consists of a cluster of narrow, tightly meshed capillaries which appear to radiate from a central focus at which a feeding arteriole enters at the posterior wall of the capillaries.)

Obviously, progression of a sharply defined wavefront is more easily tracked through the capillary network than an ill-defined one. Furthermore, if the bolus volume is small enough to essentially clear the underlying vascular layers by the time it enters the choriocapillaris, then images of the dye-filled capillaries will be of higher contrast than when significant fluorescence from beneath is simultaneously present.

Unfortunately, neither of the above conditions is readily produced by intravenous injection, even though passage of a dye bolus through the choroid can be optimized by appropriate injection technique. As a consequence, it is extremely difficult to isolate choriocapillaris dye filling in raw ICG fluorescence angiograms even when they are recorded at high speed. Therefore, there is a need for a method that will make it possible to extract information about choriocapillaris filling from venous-injection ICG dye angiograms.

Despite their inability to provide complete information about the choriocapillaris, ICG fluorescence angiograms of the choroidal circulation can delineate aberrant vascular structures in the choroid which significantly diminish vision. Age-Related Macular Degeneration (ARMD) is the leading cause of significant visual impairment in the elderly. This disease is frequently characterized by development of choroidal neovascularization (CNV) membranes which invade the sub-retinal space, resulting in displacement of the sensory retina, and often blocking of the visual pathway as a result of subsequent hemorrhage.

Treatment of ARMD is primarily by laser photocoagulation of the neovascular membrane. This treatment, however, is successful to the extent that the membrane can be accurately mapped; this is because such membranes are (by definition) in the macular area and often encroach on the fovea. Inappropriate application of photocoagulation can easily result in destruction of high acuity vision, and/or in accelerated growth of the CNV.

Diagnosis of and treatment of ARMD rely heavily upon interpretation of angiograms (both fluorescein and ICG). Frequently, the morphology of CNV lesions is such that the membranes appear in fluorescein angiograms as little more than fuzzy blurs, if at all, especially when the membrane lies beneath a cirrus detachment. Moreover, today it is recognized that for a class of CNV, referred to as "occult-CNV" ICG angiograms provide necessary treatment data which sodium fluorescein angiograms cannot.

A further major difficulty in utilizing ICG angiograms when applying laser photocoagulation therapy is that the retinal vascular landmarks upon which the surgeon must depend when aiming the laser are often missing from the ICG angiograms. The usual approach to resolving this problem is to make, during a separate setting, color photographs of the fundus and sodium fluorescein angiograms of the same eye of the patient; it is then necessary to attempt to superimpose the choroidal ICG angiogram and the retinal photograph or retinal fluorescein angiogram. This technique often fails due to the inability to precisely align the eye in exactly the same manner during each of the two angiographic procedures. Nevertheless, very accurate alignment (within as little as 50 microns on the retina) is vital to safely apply laser photocoagulation near the fovea and, at the same time, assure no significant permanent damage to the fovea itself.

Therefore, there exists a need-for new methods and devices to permit both better visualization of aberrant vascular structures such as CNV and safer and more accurate laser photocoagulation to rid the eye of such structures and improve vision.

SUMMARY OF THE INVENTION

The method of the invention is based on the premises that dye-filling of the choriocapillaris is more rapid—being pulsatile—than dye-filling of the underlying larger diameter vessels and that fluorescence from these two overlapping layers is additive. The premise regarding the velocity of blood in the choriocapillaris runs contrary to conventional wisdom regarding the relationship between blood velocities in parent and daughter vessels in most vascular beds.

In a nutshell, the invention consists of recognizing that pixel-by-pixel subtraction of an image from a succeeding image in an ICG angiographic sequence of images forms a resultant image sequence which shows fluorescence arising only from structures where the most rapid movement of blood occurs, i.e., in the choriocapillaris vessels.

This subtraction enhancement method of the invention makes it possible to extract information about choriocapillaris dye filling by taking advantage of the differences in large vessel and choriocapillaris blood flow rates which naturally exist. Instead of distinguishing choroidal layers by temporal sequence of dye bolus appearance, it is dye filling rates which serve to separate them.

Implementation of the invention depends only upon configuring an existing fundus camera system to have sufficient temporal resolution and magnification of fundus structure. The described method was applied to high-speed ICG fluorescence angiograms to emphasize information about choriocapillaris hemodynamics.

In order to better visualize CNV and facilitate treatment of ARMD, however, the invention consists of a modified fundus camera with a polarizing filter in front of the excitation light source and an analyzing polarizer in front of the video camera. ICG dye fluorescence emanating from the fundus of the eye includes a significant component of polarized light, and rotation of the analyzer filter results in unwanted fluorescence (i.e., that not associated with vascular structures, but rather associated with scattered light) being suppressed to the extent that the underlying CNV can be better visualized. This particular process affects the unprocessed, raw angiographic images in that it improves the signal-to-noise content of the individual angiographic images; subsequently, the subtracted raw images result in a clearer resultant image.

Once the aberrant vascular structure has been visualized and delineated by the polarization and subtraction methods but before laser photocoagulation therapy can begin, the surgeon must be assured that she can properly aim the laser. The invention further results from the usual practice of performing fluorescein angiography prior to performing ICG angiography and makes use of the fact that the fluorescein dye remains within the retinal vasculature for more than one hour.

The invention utilizes an ICG fundus camera which has an integrating sphere coupled to light sources for excitation of both ICG and sodium fluorescein dye fluorescences and which uses a gatable charge-coupled device (CCD) video camera to capture the angiographic images. Light input to the integrating sphere is via two fiber optic cables each connected to one of two light sources. One source is laser output at the wavelength needed to excite sodium fluorescein dye (480 nm, i.e., a frequency-doubled Nd-Yag); it is also recognized that a shuttered, filtered incandescent light source can be used in place of a frequency-doubled laser. The other source is a diode laser output for excitation of ICG dye (805 nm).

As ICG dye transits through the choroidal circulation, the gated video camera records images of the ICG dye by causing the 805 nm laser diode to fire in synchrony with the video camera. Appropriate programming of the camera and light sources are configured such that at regular intervals (e.g., every eighth image) the 480 nm light source is fired and, simultaneously, an appropriate change is made in the barrier filter in front of the video camera.

To use the every-eighth-frame example, a barrier filter chain is implemented simply by placing a rotating disk containing eight filters in front of the video camera. This filter wheel turns in synchrony with the camera firings such that every eighth frame corresponds to a positioning of the sodium fluorescein barrier filter in front of the camera. Because the sequence of angiograms is made at high speeds (approximately 15–30 images/second), eye movements between successive images is insignificant, making precise registration of images trivial. Thus, the invention provides the ability to precisely superimpose the retinal vessel landmarks contained in sodium fluorescein angiograms on the delineated CNV lesions in the ICG angiograms, as needed by the surgeon to accurately focus a laser for treatment.

DETAILED DESCRIPTION OF THE PREFERRED EMBODIMENT

Repeated real-time observations have shown that during ICG dye transit, after the large choroidal arteries fill, there is a rapidly pulsating faint and diffuse fluorescence superimposed over the steady fluorescence of the large vessels at the posterior pole. These pulsations appear to occur at a greater frequency than the heart rate, and they appear less obvious by the time the large choroidal veins are filled. Subsequent frame-by-frame analysis of the angiograms, however, indicate that the greater-than-heart-rate frequency is a perceptual phenomenon resulting from the out-of-phase pulsatile filling of individual lobules, all at near-heart-rate frequency.

Unfortunately, not enough is known yet about details of choriocapillaris hemodynamics to account with certainty for the observed more rapid fluorescence intensity changes in the choriocapillaris than in the larger underlying vessels, but the most likely reason is that choriocapillaris blood flow velocity is greater than that through the underlying choroidal vessels. The invention is based on the premises that the fluorescence intensities of ICG-filled choriocapillaris and underlying vessels are additive and that there are detectable differences in the rates of change of fluorescence intensities emanating from the choriocapillaries and the underlying choroidal vessels as they fill with dye.

Although the average cross-sectional diameter of the choriocapillaris is much smaller than that of the underlying arterial and venous vessels which feed and drain them, it appears that fluorescence from the two vascular layers is additive. ICG fluorescence additivity was demonstrated by creating a stair-step wedge of overlapping thin layers of heparinized blood containing ICG dye (0.03 mg/ml); each step was formed by a thin layer of the blood sandwiched between two microscope slide coverglasses.

Figure 1A:
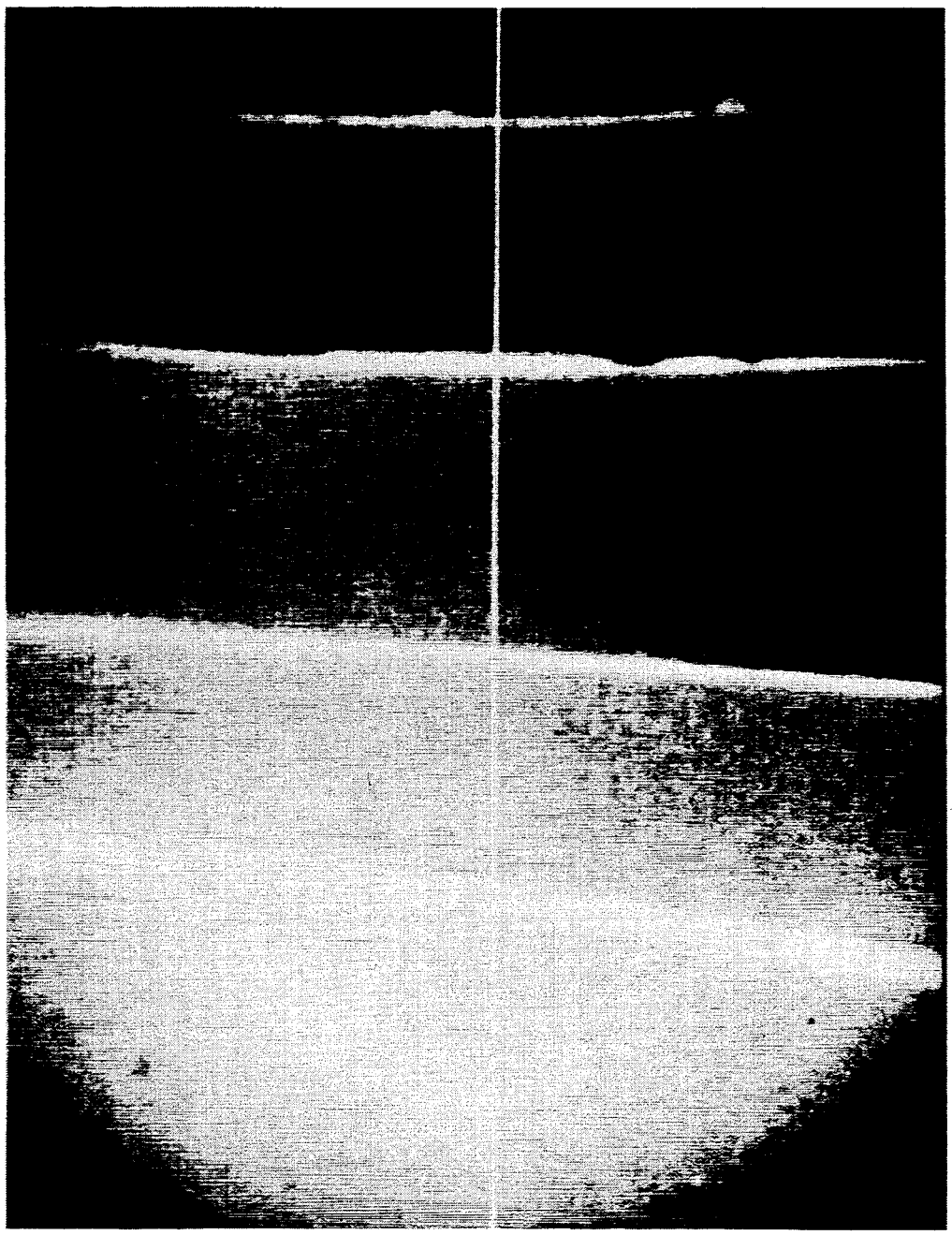
FIG. 1, consisting of FIGS. 1a and 1b, illustrates an ICG fluorescence image of layers of ICG-stained blood to demonstrate fluorescence additivity and a graph produced from the image, respectively.
Figure 1B:
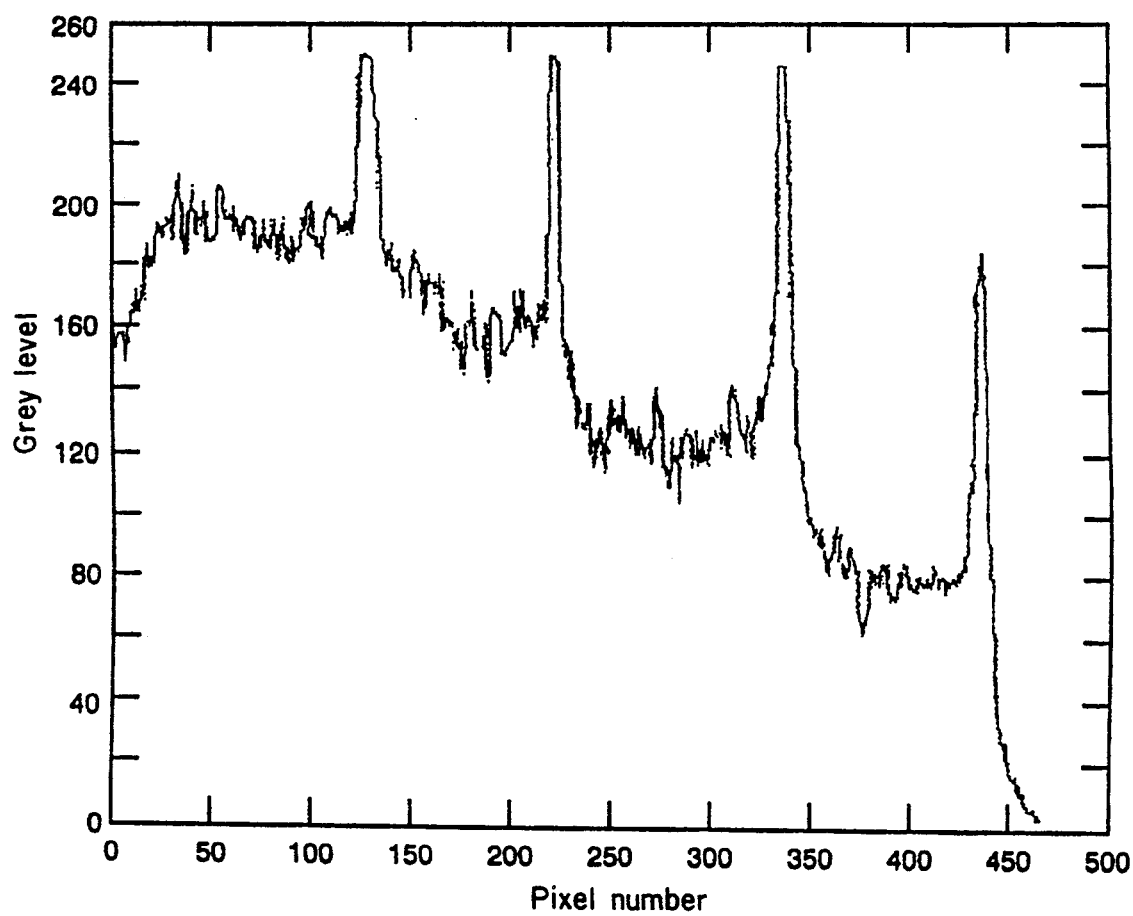

FIG. 1a shows an ICG fluorescence image of the stair steps. The horizontal white line through the center of the image indicates the path along which image pixel brightness (i.e., grey level) was measured to produce the graph in FIG. 1b, demonstrating stepwise increase in fluorescence as the number of overlapping blood layers increased.

Figure 2A:
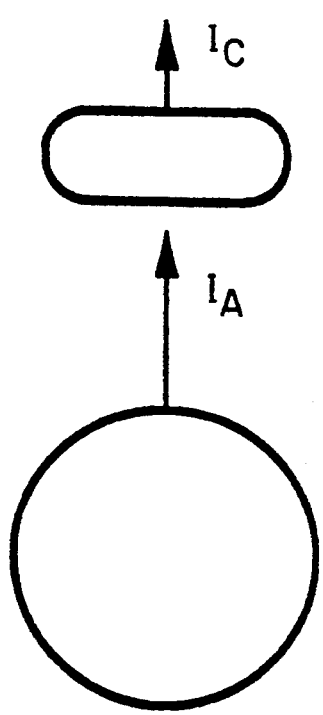
FIG. 2, consisting of FIGS. 2a and 2b, illustrates schematically the brightness of fluorescent light emitted by two different blood vessels at times $t_1$ and $t_2$, respectively.
Figure 2B:
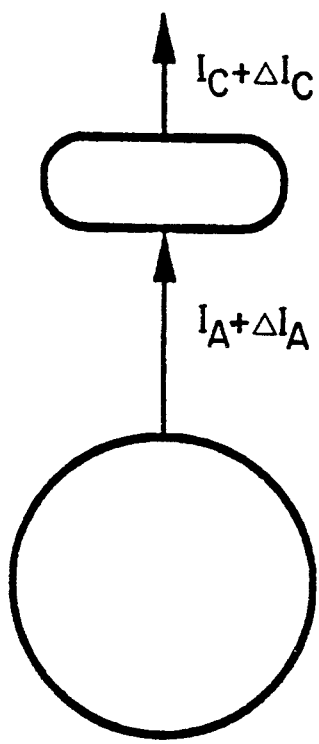

The greater rate of change in dye fluorescence intensity in choriocapillaries than in the larger underlying vessels is shown schematically in FIGS. 2a and 2b. In FIG. 2a, the brightness of a large diameter vessel and an overlying choriocapillaris vessel (both in cross-section) are indicated as vectors, $I_A$ and $I_C$, respectively. The fluorescent light emitted by both is detected at time $t_1$ by a light sensor, S. In FIG. 2b, the status of the same two vessels and sensor is shown at later time $t_2$, where $\Delta I_A$ and $\Delta I_C$ are respectively the incremental increases in brightness of the two vessels. Therefore, the total brightness detected by the sensor at $t_1$ is:

$$S_{t1} = I_A + I_C$$

At time $t_2$, the total brightness detected is:

$$S_{t2} = I_A + I_C + \Delta I_A + \Delta I_C$$

The change in total detected brightness which occurred between $t_1$ and $t_2$, $\Delta S$, then is:

$$\Delta S = S_{t2} - S_{t1} = \Delta I_C + \Delta I_C$$

But since $\Delta I_A << \Delta I_C, \Delta S = \Delta I_C.$

Figure 3A:
FIG. 3, consisting of FIGS. 3a, 3b, 3c and 3d, are, in 3a and 3b, ICG fluorescence images showing a 50 degree field of view centered on the macula of a right eye; the images were made 1/15 second apart.
FIG. 3c is the result of subtracting the image of FIG. 3a from the image of FIG. 3b.
FIG. 3d is simply an enlargement of FIG. 3c.
Figure 3B:
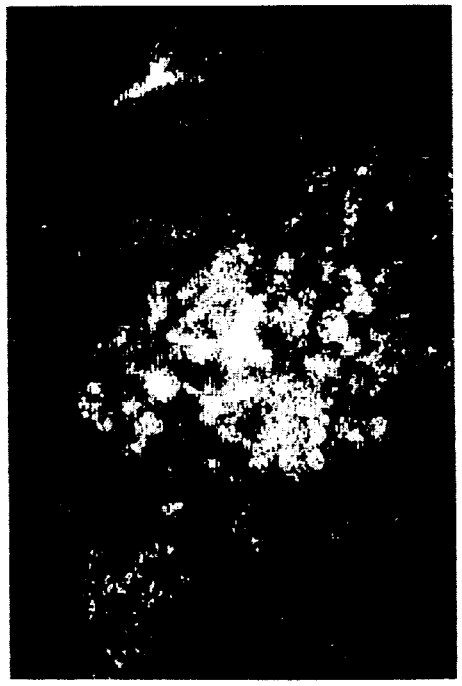
Figure 3C:
Figure 3D:

In other words, the small change in the combined brightness of the overlapping capillary and large vessel which occurs during a short time interval is virtually all attributable to the choriocapillaris vessel. This phenomenon can be demonstrated by the method of the invention, i.e., by subtracting, pixel for pixel, an image in a high-speed ICG fluorescence angiogram sequence from a succeeding image, as demonstrated in FIGS. 3a–d. FIGS. 3a and 3b are angiographic images made 1/15 second apart. FIG. 3c is the result of subtracting those two images, and FIG. 3d is simply an enlargement of FIG. 3c.

Note that in the resultant image (FIG. 3c or 3d) lobular structures are seen which were not apparent in either of the original images (FIG. 3a or 3b). Also, instead of the dye-filled retinal arteries seen in the original images, only a dye wavefront representing the movement of additional dye into the retinal arteries near the disc is seen in the resultant image. Of course, the more spatially well defined the dye bolus, the more dramatic is the effect of the invention. Not all intravenously injected dye boluses produce as dramatic results as were achieved in this example, but in each case there is enhancement of the choriocapillaris component of fluorescence. Note, the subtraction method of the invention is intended to operate by subtracting the image from any succeeding image.

To test the method of the invention, five normal rhesus monkeys between two and three years of age were used. For each observation a monkey was immobilized by intramuscular injection of ketamine hydrochloride (10 to 15 mg/kg), intubated, and then maintained lightly anesthetized with halothane; mydriasis was induced by topical application of 1% tropicmide. Small boluses (about 0.05 ml) of ICG dye (12.5 mg/ml) were injected through a catheter inserted in the greater saphenous vein and immediately followed by a 2.0 ml saline flush. Passage of dye through the choroidal vasculature was detected using a modified Zeiss fundus camera and directly digitally recorded by PC-based video frame-grabbers. At least three angiographic studies of the same eye were performed on different days for each monkey.

Figure 4:
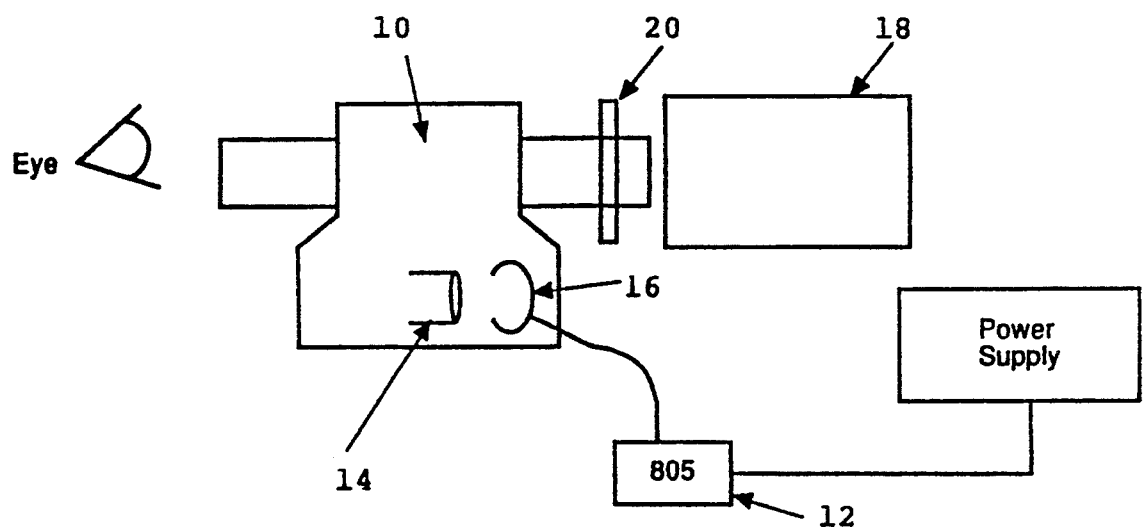
FIG. 4 illustrates a fundus camera system modified to provide the angiograms seen in FIGS. 3a and 3b.

In the above test, as shown in FIG. 4, the usual fundus camera 10 was modified by replacing the xenon flash tube light source with an 805 nm wavelength laser diode 12 coupled to the fundus camera's illumination optics 14 via a small integrating sphere 16 whose exit port was located at the position normally occupied by the flash tube arc. The fundus camera's usual means for receiving images, i.e., the photographic film camera, was replaced with an infrared sensitive vidicon tube (model 4532URI Ultracon, Burle Industries) 18 (a charge-coupled device could be used instead of the vidicon tube), in front of which an 807 nm wavelength cut-on filter 20 was placed to exclude the excitation laser light while admitting ICG dye fluorescence light. Choroidal dye transit was recorded in thirty-two consecutive video angiographic images at a rate of 30 or 15 frames per second by two digital frame grabbers (model 2861-60, Data Translation) (not shown) installed in a personal computer (Compaq, model 386/25e) (not shown).

FIG. 5 summarizes the angiographic findings obtained in the above test by applying the image subtraction method of the invention. In this example case, each image in a 15 frames/second ICG angiographic sequence was subtracted from the image immediately following it; the images in FIG. 5 were selected from the resulting sequence of subtracted images.

Figure 5B:
FIG. 5, consisting of FIGS. 5a, 5b, 5c and 5d, illustrates four images of a left eye selected from a sequence of images produced by the subtraction method of the invention.
Figure 5D:
Figure 5A:
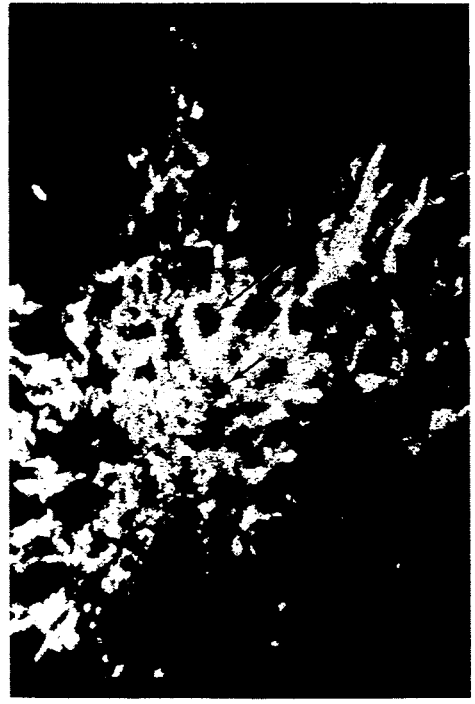

Dye first enters the macular area of the choriocapillaris which lies temporal to and above the points at which the short posterior ciliary arteries enter the eye (FIG. 5a). A lobular pattern can be seen in the center of the angiogram, particularly just nasal to the center; here a cluster of unfilled lobules is shown (arrows). 0.133 seconds later (FIG. 5b) the entire central area is completely filled, although two smaller clusters of late-filling lobules may be seen superior to the center (arrows). Choriocapillaris filling progresses almost radially from the macular region. By close inspection of this image, faint loss of fluorescence around lobules can be seen; these likely correspond to choriocapillaris drainage channels.

Figure 5C:
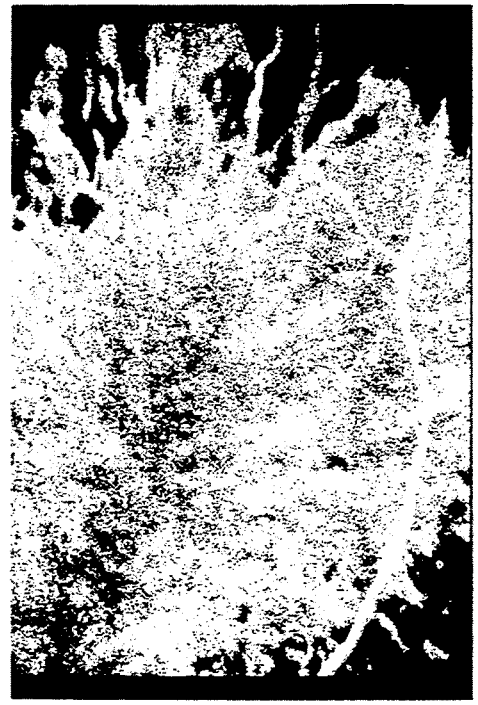

FIG. 5c is 0.200 seconds later than FIG. 5b. It indicates that the radially oriented wave of choriocapillaris dye filling has been completed, and dye distribution at the posterior pole region appears fairly uniform. This image indicates that the first wave of dye filling is complete within the center of the macular region, as indicated by the appearance of relatively hypo-fluorescent areas which were hyper-fluorescent in FIG. 5a.

In FIG. 5d, 0.133 seconds later, it appears that the first wavefront of dye filling has reached the peripheral region; at this stage, FIG. 5d is nearly a complete reverse contrast image of FIG. 5a.

The wavefront of dye filling traveled radially from the macular region to the periphery of the 30 degree field of view in approximately 0.466 seconds. This overall filling pattern was present in each eye observed, and details of the filling patterns were remarkably consistent from observation to observation for each subject eye.

ICG fluorescence angiography gradually is being used more frequently by both researchers and clinicians to investigate the choroidal circulation. Clearly, as such new tools are applied in a variety of new ways to studying the choroid, old concepts about it and its physiology will be revisited, and some will change or give way to entirely new concepts. Fortunately, some approaches to analyzing choroidal angiograms like the subtraction method of the invention described above may be applied both in animal and in human clinical research with complete safety, perhaps hastening a better understanding of choroidal blood flow in health and disease.

ICG fluorescence angiography is used in the diagnosis and treatment of ARMD; however, as noted above, the difficulty arises in attempting to accurately map choroidal neovascularization (CNV). The invention lies in recognizing that fluorescence arising from a dye molecule contains information about the processes that take place within the molecule during the time between excitation and emission of light by the molecule. Moreover, fluorescence of molecules can be affected by the characteristics of the substances to which the molecule is bound and by the character of the binding which has taken place.

For example, in the case of ICG dye in the vasculature of an eye containing CNV, the dye may bind with greater affinity to neovascular endothelium than to established endothelium. In such a case, fluorescence arising from those bound dye molecules may be substantially different from fluorescence associated with ICG dye molecules which may be bound to other types of protein in the cirrus fluid or from ICG fluorescent light simply scattered by the presence of protein molecules within the cirrus fluid. In either event, ellipsometry is an appropriate tool for improving the visualization of CNV.

Figure 6:
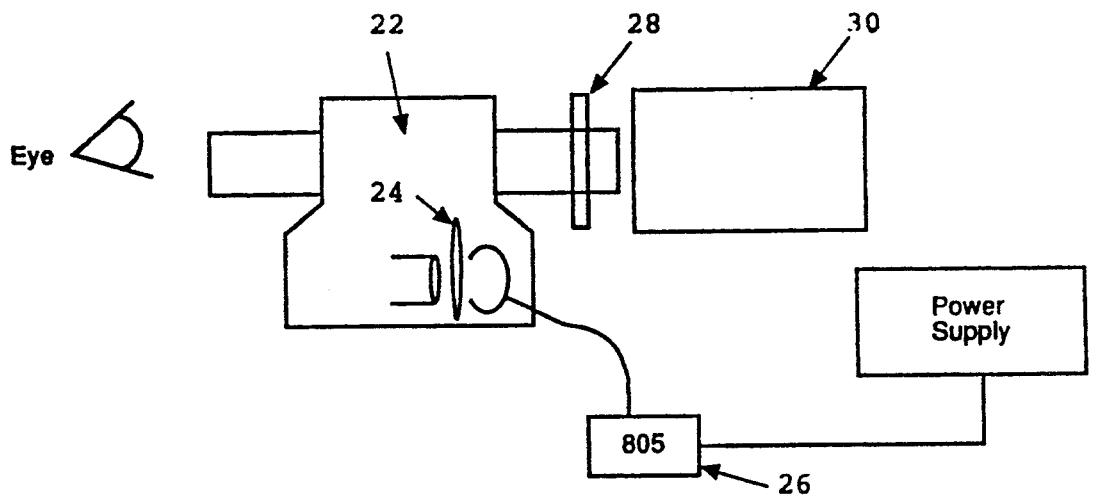
FIG. 6 illustrates a fundus camera system modified to suppress unwanted fluorescence.

The invention then, as shown in FIG. 6, is a modified fundus camera 22 with a polarizing filter 24 in front of the excitation light source 26 and an analyzing polarizer 28 in front of the video camera 30. ICG dye produces a high degree of polarized ability, and rotation of the analyzer filter results in the fluorescence from the cirrus fluid being suppressed to the extent that the underlying CNV can be better visualized. This particular process affects the unprocessed, raw angiographic images in that it improves the signal-to-noise content of the individual angiographic images; subsequently, the subtracted raw images result in a clearer resultant image.

Once an aberrant vascular structure such as CNV is clearly delineated, it can be treated using laser photocoagulation therapy; however, as noted above, aiming the laser properly requires superimposing an ICG angiogram and a retinal photograph or retinal fluorescein angiogram. The invention results from the usual practice of performing fluorescein angiography prior to performing ICG angiography making use of the fact that the fluorescein dye remains within the retinal vasculature for quite long periods of time (more than one hour). Therefore, if one configures an ICG fundus camera in such a way that during the course of obtaining ICG angiograms, a fluorescein angiogram can be obtained (within fractions of a second of obtaining a previous and succeeding ICG angiogram), no significant movement of the eye can take place. This means that the intervening fluorescein angiogram would, by definition, precisely register with the ICG angiograms.

Figure 7:
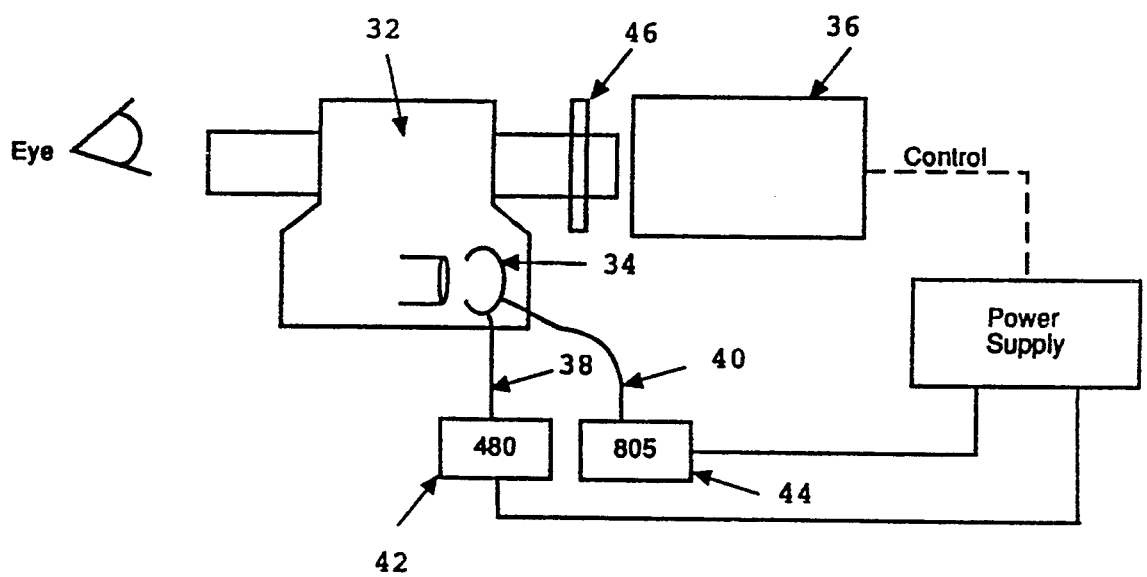
FIG. 7 illustrates a fundus camera system modified to provide superimposed angiograms.

As shown in FIG. 7, the invention utilizes an ICG fundus camera 32 which has an integrating sphere 34 coupled to light sources for excitation of ICG dye fluorescence and which uses, as an image receiving means, a gatable video camera 36 (preferably CCD) to capture the angiographic images. Light input to the integrating sphere is via two fiber optic cables 38, 40, each connected to one of two light sources 42, 44; one source 42 output is at the wavelength needed to excite sodium fluorescein dye (480 nm) and the other source 44 output for excitation of ICG dye (805 nm).

As ICG dye transits through the choroidal circulation, the gated video camera 36 records images of the ICG dye by causing the 805 nm laser source 44 to fire in synchrony with the video camera 36. Appropriate programming of the camera and light sources are configured such that at regular intervals (e.g., every eighth image) the 480 nm source 42 is fired, and simultaneously an appropriate change is made in the barrier filter 46 in front of the video camera.

To use the every-eighth frame example, the barrier filter chain is implemented simply by placing a rotating disk containing eight filters in front of the video camera. This filter wheel turns in synchrony with the camera firings such that every eighth frame corresponds to a positioning of the fluorescein barrier filter in front of the camera. Thus, the invention provides the ability to precisely superimpose angiograms needed by the surgeon in order to accurately aim a laser photocoagulation beam.

I claim:

1. A method for visualizing a first layer of blood vessels from a second layer of blood vessels, the first layer being coextensive with the second layer, in a sequence of angiographic images, wherein the rate of change of fluorescence emitted from the first layer is greater than the rate of change of fluorescence emitted from the second layer, the method comprising the steps of:
   injecting intravenously a fluorescent dye, the dye filling the first and second layers of blood vessels;
   exciting the dye thereby causing a fluorescence to be emitted from the first and second layers of blood vessels;
   taking a sequence of angiographic images of the emitted fluorescence; and
   subtracting an image in the sequence of angiographic images from a succeeding image thereby forming a resultant image, the resultant image showing the fluorescence emitted from the first layer of blood vessels.

2. The method as recited in claim 1, wherein the first layer of blood vessels comprises a choriocapillaris and the second layer of blood vessels comprises a plurality of underlying choroidal vessels, the choroidal vessels being larger in diameter than the vessels of the choriocapillaris.

3. The method as recited in claim 1, wherein the sequence of angiographic images are taken using an indocyanine green (ICG) dye.

4. The method as recited in claim 1, wherein the sequence of angiographic images is taken at a speed of greater than 14 frames per second.

5. The method as recited in claim 1, wherein the sequence of angiographic images is taken at a speed of greater than 29 frames per second.

6. The method as recited in claim 1, wherein the image is subtracted from the succeeding image, pixel by pixel, to form the resultant image.

7. The method as recited in claim 1, wherein the subtracting step comprises the steps of:
   digitizing the image in the sequence of angiographic images; and
   subtracting the image from the succeeding image, pixel by pixel, to form the resultant image.

8. A device for forming the resultant image of claim 1, comprising:
   a fundus camera for taking a sequence of angiographic images of an eye;
   an integrating sphere coupled to illumination optics in the fundus camera;
   a light source coupled to the integrating sphere;
   a means for receiving the sequence of angiographic images from the fundus camera; and
   a means for subtracting the image from the succeeding image in the sequence of angiographic images received from the receiving means.

9. The device as recited in claim 8, further comprising a filter, the filter being placed between the fundus camera and the receiving means to admit fluorescence and exclude light from the light source.

10. The device as recited in claim 8, the subtracting means further comprising a means for digitizing the sequence of angiographic images received from the receiving means.

11. The device as recited in claim 8, wherein the light source comprises a laser.

12. The device as recited in claim 11, wherein the laser has a wavelength of 805 nm.

13. The device as recited in claim 8, wherein the receiving means comprises a vidicon tube.

14. The device as recited in claim 8, wherein the receiving means comprises a charge-coupled device.

15. A method for visualizing the choriocapillaris from the other blood vessels in the choroid in a sequence of ICG angiographic images comprising the steps of:
   injecting intravenously a fluorescent dye, the dye filling the choriocapillaris and the other blood vessels in the choroid;
   exciting the dye thereby causing a fluorescence to be emitted from the choriocapillaris and the other blood vessels in the choroid;
   taking a sequence of angiographic images of the emitted fluorescence; and
   subtracting an image from a succeeding image, pixel by pixel, thereby forming a resultant image, the resultant image showing fluorescence emitted from the choriocapillaris.

16. The method as recited in claim 15, further comprising the step of digitizing the image and the succeeding image before the subtracting step.

17. A method for improving the visualization of choroidal neovascularization (CNV) during an angiography comprising the steps of:
   injecting intravenously a fluorescent dye, the dye filling the vasculature of an eye;
   exciting the dye thereby causing a fluorescence to be emitted from the vasculature;
   suppressing fluorescence other than fluorescence from the CNV using a polarizing filter placed in a fundus camera; and
   taking an angiographic image of the fluorescence from the CNV.

18. A device for improving the visualization of choroidal neovascularization (CNV) comprising:
   a fundus camera;

an excitation light source coupled to the fundus camera;

a polarizing filter placed in front of the light source;

a means for receiving images from the fundus camera; and an analyzing polarizer placed between the receiving means and the fundus camera.

19. The device as recited in claim 18, wherein the receiving means comprises a video camera.

20. A device for providing superimposed angiograms of an eye comprising:

a fundus camera for taking angiographic images of the eye;

an integrating sphere coupled to the fundus camera;

two light sources, each light source connected to the integrating sphere by a fiber optic cable and operating at a different wavelength to excite a first dye and a second dye causing a different fluorescence to be emitted from each dye;

a means for receiving the angiographic images of the eye from the fundus camera; and a filter means between the fundus camera and the receiving means, the filter means containing at least two filters, a first filter to pass the fluorescence from the first dye and a second filter to pass the fluorescence from the second dye;

wherein by alternating the first and second filters in synchrony with the firing of the light sources and the receiving means different angiograms are taken, the angiograms being superimposed thereby.

21. The device as recited in claim 20, wherein the light sources comprise a first laser and a second laser.

22. The device as recited in claim 21, wherein the first laser has a wavelength of 805 nm and the second laser has a wavelength of 480 nm.

23. The device as recited in claim 20, wherein the light sources comprise a laser and a shuttered, filtered incandescent lamp.

24. The device as recited in claim 20, wherein the receiving means comprises a gatable video camera.

25. The device as recited in claim 20, wherein the receiving means comprises a charge-coupled device.

26. The device as recited in claim 20, wherein the filter means comprises a rotating barrier filter wheel.

27. A method for providing superimposed angiograms comprising the steps of:

injecting a first dye followed by a second dye thereby having two dyes present simultaneously;

exciting the two dyes alternately with a first light source and a second light source, each light source having a different wavelength thereby alternately producing two different fluorescences; and recording the alternately produced fluorescences to provide superimposable angiograms.

28. The method as recited in claim 27, wherein the first dye comprises sodium fluorescein and the second dye comprises indocyanine green.

29. The method as recited in claim 27, wherein the first light source comprises a laser having a wavelength of 805 nm and the second light source comprises a laser having a wavelength of 480 nm.

30. The method as recited in claim 27, wherein the first light source comprises a laser having a wavelength of 805 nm and the second light source comprises a shuttered, filtered incandescent lamp producing a wavelength of 480 nm.

* * * * *